United States Patent
Choi et al.

(10) Patent No.: US 12,168,065 B2
(45) Date of Patent: Dec. 17, 2024

(54) COSMETIC COMPOSITION FOR UV-PROTECTION THAT INCREASES UV PROTECTION EFFICIENCY BY MEANS OF UV LIGHT

(71) Applicant: LG HOUSEHOLD & HEALTH CARE LTD., Seoul (KR)

(72) Inventors: Min-Sung Choi, Seoul (KR); Kyung-Hee Song, Seoul (KR); Hyeong-Jin Cho, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 575 days.

(21) Appl. No.: 17/433,543

(22) PCT Filed: Dec. 6, 2019

(86) PCT No.: PCT/KR2019/017182
§ 371 (c)(1),
(2) Date: Aug. 24, 2021

(87) PCT Pub. No.: WO2020/175772
PCT Pub. Date: Sep. 3, 2020

(65) Prior Publication Data
US 2022/0151893 A1 May 19, 2022

(30) Foreign Application Priority Data

Feb. 27, 2019 (KR) .................. 10-2019-0023391
Mar. 29, 2019 (KR) .................. 10-2019-0037278
Aug. 29, 2019 (KR) .................. 10-2019-0106892
Aug. 29, 2019 (KR) .................. 10-2019-0106893

(51) Int. Cl.
*A61K 8/37* (2006.01)
*A61K 8/06* (2006.01)
*A61K 8/31* (2006.01)
*A61Q 17/04* (2006.01)

(52) U.S. Cl.
CPC .............. *A61K 8/37* (2013.01); *A61K 8/062* (2013.01); *A61K 8/31* (2013.01); *A61Q 17/04* (2013.01); *A61K 2800/522* (2013.01); *A61K 2800/591* (2013.01)

(58) Field of Classification Search
CPC . A61K 8/37; A61K 8/062; A61K 8/31; A61K 2800/522; A61K 2800/591; A61Q 17/04
See application file for complete search history.

(56) References Cited

U.S. PATENT DOCUMENTS

| | | |
|---|---|---|
| 4,562,067 A | 12/1985 | Hopp et al. |
| 2003/0185772 A1 | 10/2003 | Kouzuki et al. |
| 2013/0022560 A1 | 1/2013 | Schlifkeposchalko |
| 2014/0140940 A1 | 5/2014 | Thaden et al. |
| 2016/0338937 A1 | 11/2016 | Amazaki |

FOREIGN PATENT DOCUMENTS

| | | |
|---|---|---|
| JP | 2002-179525 A | 6/2002 |
| JP | 2002-284622 A | 10/2002 |
| JP | 2017-88599 A | 5/2017 |
| KR | 10-2009-0069370 A | 7/2009 |
| KR | 10-2011-0054736 A | 5/2011 |
| KR | 10-2011-0078358 A | 7/2011 |
| KR | 10-2013-0026209 A | 3/2013 |
| KR | 10-2015-0011887 A | 2/2015 |
| KR | 10-2016-0013032 A | 2/2016 |
| KR | 10-2026658 B1 | 9/2019 |
| WO | WO 2007/144670 A1 | 12/2007 |
| WO | WO 2009/069933 A2 | 6/2009 |
| WO | WO 2011/130358 A2 | 10/2011 |

OTHER PUBLICATIONS

Daily Sun Block SPF 39PA++ (ID: 1394186), Mintel GNPD [online], Sep. 2010, [Search date: Jun. 27, 2022], https://www.gnpd.com.
Mid-Day Blue Sun LotionSPF 40 PA++ (ID: 5520499), Mintel GNPD [online], Mar. 2018, [Search date: Jun. 27, 2022], https://www.gnpd.com.
Sun Block Cream SPF 30PA++ (ID: 1808102), Mintel GNPD [online], Jun. 2012, [Search date: Jun. 27, 2022], https://www.gnpd.com.
Whitening Sun ProtectCream UV SPF 50 PA +++ (ID: 5985425), Mintel GNPD [online], Sep. 2018, [Search date: Jun. 27, 2022], https://www.gnpd.com.
International Search Report (PCT/ISA/210) issued in PCT/KR2019/017182 mailed on Mar. 26, 2020.

*Primary Examiner* — Shirley V Gembeh
(74) *Attorney, Agent, or Firm* — Birch, Stewart, Kolasch & Birch, LLP (57) ABSTRACT

The present invention relates to a cosmetic composition for UV protection and, specifically, to a cosmetic composition for UV protection comprising: a sunscreen having a methoxycinnamate structure; and a specific weight of polar oil. The cosmetic composition for UV protection of the present invention significantly increases UV protection efficiency when exposed to UV light and has a remarkably excellent skin feel.

15 Claims, 4 Drawing Sheets

COSMETIC COMPOSITION FOR UV-PROTECTION THAT INCREASES UV PROTECTION EFFICIENCY BY MEANS OF UV LIGHT

TECHNICAL FIELD

The present application claims priority to Korean Patent Application No. 10-2019-0023391 filed on Feb. 27, 2019, Korean Patent Application No. 10-2019-37278 filed on Mar. 29, 2019, Korean Patent Application No. 10-2019-0106892 filed on Aug. 29, 2019 and Korean Patent Application No. 10-2019-0106893 filed on Aug. 29, 2019 in the Republic of Korea, the disclosures of which are incorporated herein by reference. The present disclosure relates to a cosmetic composition for ultraviolet (UV) protection which shows a boost in sun protection efficiency by UV light.

BACKGROUND ART

Ultraviolet (UV) light irradiated from the sunlight functions as a main cause of erythema, edema, freckle, or the like, on the skin, or skin cancer. Recently, active studies have been conducted about various types of skin diseases caused by ultraviolet light. In general, UV is classified, depending on wavelength, into UV-C having a wavelength of 200-280 nm, UV-B having a wavelength of 280-320 nm, and UV-A having a wavelength of 320-400 nm. Among them, it is known that UV-C does not arrive at the ground surface and disappears, while passing through the ozone layer, UV-B infiltrates to the skin epidermis to cause erythema, freckle, edema, or the like, and UV-A infiltrates to the derma to cause skin cancer, to accelerate skin aging, such as wrinkles and melanin formation, and to cause skin irritation. A strong relationship between exposure to the sunlight and human skin cancer has been demonstrated through many epidemiological studies.

As a result of the above-mentioned risks related with exposure to the sunlight, public interest in sun protection products has been increased, resulting in the launch of various types of sun protection products having different sun protection factors (SPF). The sun protection products include inorganic sunscreens, such as titanium dioxide or zinc oxide, or organic sunscreens, such as ethylhexyl methoxycinnamate, ethylhexyl salicylate, octocrylene, butylmethoxydibenzoyl methane, bis-ethylhexyloxyphenol-methoxyphenyl triazine or diethylaminohydroxybenzoyl-hexyl benzoate, so that they may have a high SPF value.

Sun protection cosmetic products may undergo a decrease in sun protection efficiency by UV light. Particularly, a sunscreen, such as ethylhexyl methoxycinnamate, isoamyl p-methoxycinnamate or cinoxate, having a methoxycinnamate structure has a problem of degradation of UV light absorbing efficiency because its trans structure is converted into a cis structure by UV light. When sun protection efficiency is decreased, it is not possible to protect UV light effectively, resulting in skin aging or various skin diseases. In addition, as outdoor activities increase and the skin is exposed to the sunlight for a longer time, the inconvenience of having to reapply a sun protection product several times may be generated. To solve the above-mentioned problems, there is a need for developing a method for preventing the efficacy degradation of a sunscreen having a methoxycinnamate structure in a cosmetic composition for UV protection, or a method for enhancing the effect even with the same amount.

DISCLOSURE

Technical Problem

The present disclosure is directed to providing a cosmetic composition for UV protection, which solves the problem of degradation of sun protection efficiency upon the exposure of a sunscreen having a methoxycinnamate structure to UV light and rather shows a boost in sun protection efficiency by UV light.

Technical Solution

The inventors of the present disclosure have conducted intensive studies to solve the problems of the related art, and have found that a cosmetic composition including a sunscreen having a methoxycinnamate structure shows a boost in sun protection efficiency, when it is exposed to UV light under a specific condition. The present disclosure is based on this finding.

The inventors of the present disclosure have found that a variation in content of polar oil or hydrocarbon oil in the cosmetic composition including the above-mentioned sunscreen can control the intermolecular distance of methoxycinnamate. Particularly, when the intermolecular distance is large, methoxycinnamate molecules having a trans structure may be converted into a cis structure by UV light, resulting in significant degradation of UV absorptivity. However, when the intermolecular distance is sufficiently short, various photoreaction products, including dimers, can be formed upon the exposure to UV light. In addition, $\pi$-$\pi$ staking with the formed photoreaction products causes a change in $\pi$-$\pi^*$ transition energy level, and thus the wavelength region capable of being absorbed by the sunscreen may be extended. The cosmetic composition including a sunscreen according to the present disclosure has a significantly increased absorbance in the UV-A wavelength region (320-400 nm) and UV-B wavelength region (280-320 nm), as compared to the absorbance before UV irradiation, and shows a significantly increased SPF value.

In one aspect of the present disclosure, there is provided a cosmetic composition for UV protection, including a sunscreen having a methoxycinnamate structure and polar oil. In another aspect of the present disclosure, there is provided a cosmetic composition for UV protection, including a sunscreen having a methoxycinnamate structure and hydrocarbon oil. The sunscreen having a methoxycinnamate structure may include at least one selected from the group consisting of ethylhexyl methoxycinnamate, isoamyl p-methoxycinnamate and cinoxate. The sunscreen having a methoxycinnamate structure may be used in an amount of 2-30 wt %, preferably 2-25 wt %, and more preferably 2-20 wt %, based on the total weight of the composition. When the sunscreen having a methoxycinnamate structure is used in an amount of less than 2 wt % based on the total weight of the composition, SPF is decreased by UV light. When the sunscreen having a methoxycinnamate structure is used in an amount of larger than 30 wt %, the formulation stability of the cosmetic composition may be affected adversely.

According to an embodiment, the polar oil may be ester-based oil or triglyceride, and particularly, may include at least one selected from the group consisting of cetylethyl hexanoate, caprylic/capric glycerides, phenethyl benzoate, dicaprylyl carbonate, C12-C15 alkyl benzoates and octocrylene, but is not limited thereto. The polar oil may be used in an amount of 5 wt % or less, preferably 0.01-5 wt %, and more preferably 0.05-4 wt %, based on the total weight of the composition. However, it is most preferred that the composition includes no polar oil. When the polar oil is used in an amount of larger than 5 wt %, it is not possible to realize the effect of increasing SPF by UV light.

According to an embodiment, the cosmetic composition for UV protection, including a sunscreen having a methoxycinnamate structure and polar oil according to the present disclosure may further include hydrocarbon oil. In this case, it is possible to increase the sun protection effect significantly and to provide excellent skin applicability. The hydrocarbon oil may include at least one selected from the group consisting of liquid paraffin, light liquid isoparaffin, heavy liquid isoparaffin, Vaseline, n-paraffin, mineral oil, isoparaffin, isododecane, isohexadecane, polyisobutylene, hydrogenated polyisobutylene, polybutene, ozokerite, ceresin, microcrystalline wax, paraffin wax, polyethylene wax, polyethylene/polypropylene wax, squalane, squalene, pristane and polyisoprene, but is not limited thereto.

The hydrocarbon oil may be used in an amount of 5-30 wt %, preferably 5.1-30 wt %, 5.5-30 wt %, 6-30 wt %, 6.5-30 wt %, or 7-30 wt %, based on the total weight of the composition. Preferably, the hydrocarbon oil may be used in an amount of 5-25 wt %, more preferably 5.1-25 wt %, 5.5-25 wt %, 6-25 wt %, 6.5-25 wt %, or 7-25 wt %, based on the total weight of the composition. Preferably, the hydrocarbon oil may be used in an amount of 5-15 wt %, more preferably 5.1-15 wt %, 5.5-15 wt %, 6-15 wt %, 6.5-15 wt %, or 7-15 wt %, based on the total weight of the composition. When the hydrocarbon oil is used in an amount of less than 5 wt % based on the total weight of the composition, the cosmetic composition shows an excessively stiff feeling of use, and thus cannot satisfy the fundamental quality standard of cosmetic products. When the hydrocarbon oil is used in an amount of larger than 30 wt %, the formulation stability may be affected adversely.

According to an embodiment, the cosmetic composition for UV protection according to the present disclosure may further include silicone oil. In this case, it is possible to provide an excellent effect of increasing sun protection efficiency by UV light and to assist improvement of a feeling of use. However, since silicone oil has poor compatibility with a sunscreen having a methoxycinnamate structure under the above-defined condition with a limited content of polar oil, it is not preferred to use an excessive amount of silicone oil. The cosmetic composition for UV protection according to the present disclosure includes substantially no silicone oil, and may include silicone oil in an amount of 15 wt % or less, preferably 10 wt % or less, more preferably 5 wt % or less, and even more preferably 3 wt % or less, based on the total weight of the composition. The silicone oil may be at least one selected from the group consisting of cyclotetrasiloxane, cyclopentasiloxane, cyclohexasiloxane, dimethicone, dimethiconol and phenyl trimethicone, but is not limited thereto. The sunscreen contained in the cosmetic composition according to the present disclosure, i.e. ethylhexyl methoxycinnamate or isoamyl p-methoxycinnamate, has poor compatibility with silicone oil. Therefore, when silicone oil is used in an amount of larger than 15 wt %, the cosmetic composition may show poor stability at room temperature.

According to an embodiment, the cosmetic composition for UV protection according to the present disclosure may include a sunscreen having a methoxycinnamate structure and polar oil at a weight ratio (sunscreen having a methoxycinnamate structure:polar oil) of 1:0.01-1, preferably 1:0.01-0.8, more preferably 1:0.01-0.6, even more preferably 1:0.01-0.4, particularly 1:0.01-0.2. Most preferably, the cosmetic composition for UV protection may include no polar oil. When the content of the polar oil exceeds the above-defined weight ratio, it is not possible to realize an effect of increasing sun protection efficiency by UV light.

According to an embodiment, the cosmetic composition for UV protection according to the present disclosure may include a sunscreen having a methoxycinnamate structure and hydrocarbon oil at a weight ratio (sunscreen having a methoxycinnamate structure:hydrocarbon oil) of 1:0.2-15, preferably 1:0.2-8, and more preferably 1:0.2-3. The hydrocarbon oil may be used at an adequate weight ratio to the sunscreen to improve the feeling of use of the cosmetic composition, within a range of 5 wt % or more based on the total weight of the composition. When the content of the hydrocarbon oil does not fall within the above-defined range, the effect of increasing sun protection efficiency by UV light or the feeling of use of the cosmetic composition may be degraded.

According to an embodiment, when the cosmetic composition for UV protection according to the present disclosure includes polar oil and hydrocarbon oil at the same time, it may include polar oil and hydrocarbon oil at a weight ratio (polar oil:hydrocarbon oil) of 1:1-300, preferably 1:1-200, and more preferably 1:1-100. When the weight ratio of polar oil to hydrocarbon oil does not fall within the above-defined range, the effect of increasing sun protection efficiency by UV light or the feeling of use of the cosmetic composition may be degraded.

According to an embodiment, the cosmetic composition for UV protection according to the present disclosure may further include an inorganic sunscreen. The inorganic sunscreen may include titanium dioxide, zinc oxide, iron oxide, or the like, but is not limited thereto. In addition, the cosmetic composition for UV protection according to the present disclosure may further include a moisturizing agent, a thickener, a surfactant, an oil base, a preservative, an antioxidant, alcohol, a fragrance, a pH modifier, a natural extract, or the like, but is not limited thereto.

The cosmetic composition according to the present disclosure may be formulated into any formulation prepared conventionally in the art. For example, the cosmetic composition may be formulated into solution, suspension, emulsion, paste, gel, cream, lotion, soap, surfactant-containing cleanser, oil, or the like, but is not limited thereto. Particularly, the cosmetic composition may be formulated into skin softener, nutrient skin, skin toner, nutrient cream, emulsion, cosmetic ointment, massage cream, essence, eye cream, cleansing cream, cleansing foam, cleansing water, pack, gel, makeup base, foundation, spray, powder, or the like. According to an embodiment, the cosmetic composition for UV protection according to the present disclosure may be an emulsion formulation, such as a water-in-oil (W/O) or oil-in-water (O/W) formulation.

According to an embodiment, the present disclosure provides a cosmetic composition for UV protection, including 2-30 wt % of a sunscreen having a methoxycinnamate structure, 5 wt % or less of polar oil and 5-30 wt % of hydrocarbon oil, based on the total weight of the composition. The cosmetic composition shows a significant boost in UV protection effect after UV irradiation and a significantly improved feeling of use.

The cosmetic composition for UV protection according to the present disclosure shows a significant boost in SPF value after UV irradiation. Particularly, the cosmetic composition shows a boost in SPF value of 3-80%, preferably 5-77%, as compared to the SPF value before UV irradiation. The cosmetic composition for UV protection according to the present disclosure shows an increased effect of protecting UV-A (320-400 nm) and UV-B (280-320 nm), and preferably shows a significantly increased effect of protecting UV-B, after UV irradiation.

The present disclosure also provides a method for preparing a cosmetic composition for UV protection, including a step of mixing a sunscreen having a methoxycinnamate structure with 5 wt % or less of polar oil based on the total weight of the composition. According to an embodiment, the method may further include a step of further mixing with hydrocarbon oil. The same as described above with reference to the cosmetic composition for UV protection according to the present disclosure may be applied to the method.

In another aspect, the inventors of the present disclosure have found that when the cosmetic composition including the sunscreen contains a specific content of polar oil and is prepared in an oil-in-water (O/W) formulation, the intermolecular distance of methoxycinnamate may be controlled to get closer, resulting in a boost in UV protection efficiency upon the exposure to UV light.

The present disclosure provides a cosmetic composition for UV protection, including a sunscreen having a methoxycinnamate structure and polar oil, wherein the sunscreen is isoamyl p-methoxycinnamate. The sunscreen may further include ethylhexyl methoxycinnamate, cinoxate or a mixture thereof, besides isoamyl p-methoxycinnamate. The sunscreen having a methoxycinnamate structure may be used in an amount of 2-30 wt %, preferably 2-25 wt %, and more preferably 2-20 wt %, based on the total weight of the composition. When the sunscreen having a methoxycinnamate structure is used in an amount of less than 2 wt %, SPF is reduced by UV light. When the sunscreen having a methoxycinnamate structure is used in an amount of larger than 30 wt %, the formulation stability of the cosmetic composition may be degraded.

According to an embodiment, isoamyl p-methoxycinnamate may be used in an amount of 2-30 wt %, preferably 2-25 wt %, and more preferably 2-20 wt %, based on the total weight of the composition. When isoamyl p-methoxycinnamate is used in an amount of less than 2 wt %, SPF is reduced by UV light. When isoamyl p-methoxycinnamate is used in an amount of larger than 30 wt %, the formulation stability of the cosmetic composition may be degraded.

According to an embodiment, the polar oil may be ester-based oil or triglyceride, except a sunscreen having a methoxycinnamate structure. Particularly, the polar oil may include at least one selected from the group consisting of cetylethyl hexanoate, caprylic/capric glycerides, phenethyl benzoate, dicaprylyl carbonate, C12-C15 alkyl benzoates, octocrylene and phenyl trimethicone, but is not limited thereto According to an embodiment, the content of the polar oil may be equal to or smaller than the content of isoamyl p-methoxycinnamate. In other words, the polar oil may be used in an amount of 0.01-30 wt %, preferably 0.01-25 wt %, and more preferably 0.01-20 wt %, based on the total weight of the composition. In a variant, the cosmetic composition for UV protection according to the present disclosure may include no polar oil. When the content of the polar oil is larger than the content of isoamyl p-methoxycinnamate, it is not possible to realize an effect of increasing SPF by UV light.

According to an embodiment, the cosmetic composition for UV protection according to the present disclosure may include the sunscreen having a methoxycinnamate structure and polar oil at a weight ratio (sunscreen having a methoxycinnamate structure:polar oil) of 1:0.01-7, preferably 1:0.01-0.5, and more preferably 1:0.01-0.3. In a variant, the cosmetic composition for UV protection according to the present disclosure may include isoamyl p-methoxycinnamate and polar oil at a weight ratio (isoamyl p-methoxycinnamate:polar oil) of 1:0.01-7, preferably 1:0.01-0.5, and more preferably 1:0.01-0.3. When the content of the polar oil exceeds the above-defined range of weight ratio, it is not possible to realize an effect of increasing UV protection efficiency by UV light.

According to an embodiment, the cosmetic composition for UV protection may further include nonpolar oil. Particular examples of the nonpolar oil may include hydrocarbon oil, silicone oil or a mixture thereof. When the cosmetic composition for UV protection includes hydrocarbon oil, it is possible to realize excellent skin applicability and an increased UV protection effect. The hydrocarbon oil may include at least one selected from the group consisting of isododecane, isohexadecane, mineral oil, hydrogenated polydecene and squalane, but is not limited thereto. In addition, when the cosmetic composition for UV protection further includes silicone oil, it is possible to realize an excellent effect of increasing UV protection efficiency by UV light and to improve a feeling of use. The silicone oil may be at least one selected from the group consisting of cyclotetrasiloxane, cyclopentasiloxane, cyclohexasiloxane, dimethicone, dimethiconol and phenyltrimethicone, but is not limited thereto.

The cosmetic composition for UV protection according to the present disclosure may include nonpolar oil in an amount of 20 wt % or less, preferably 15 wt % or less, more preferably 5 wt % or less, and even more preferably 3 wt % or less, based on the total weight of the composition. The nonpolar oil may be used in an amount of 0.01-20 wt %, preferably 5.0-20 wt %, or 5.1-20 wt %, based on the total weight of the composition. Preferably, the nonpolar oil may be used in an amount of 0.01-10 wt %, more preferably 5.0-10 wt %, or 5.1-10 wt %, based on the total weight of the composition. When the nonpolar oil is used in an amount of less than 0.01 wt % based on the total weight of the composition, the cosmetic composition shows an excessively stiff feeling of use and thus cannot satisfy the fundamental quality standard of cosmetic products. When the nonpolar oil is used in an amount of larger than 20 wt %, the formulation stability may be affected adversely.

According to an embodiment, the cosmetic composition for UV protection according to the present disclosure may have an emulsion formulation, preferably oil-in-water (O/W) formulation. When the cosmetic composition for UV protection according to the present disclosure is provided in an oil-in-water formulation containing a specific content of polar oil, it is possible to provide a significantly high effect of increasing UV protection efficiency after UV irradiation.

According to an embodiment, the present disclosure provides a cosmetic composition for UV protection having an oil-in-water formulation and including a sunscreen having a methoxycinnamate structure and polar oil, wherein the sunscreen includes isoamyl p-methoxycinnamate and is used in an amount of 2-30 wt % based on the total weight of the composition, and the content of the polar oil is equal to or smaller than the content of isoamyl p-methoxycinnamate. The composition shows a significantly increased UV protection effect after UV irradiation, and has a significantly improved feeling of use.

The cosmetic composition for UV protection according to the present disclosure shows a significant boost in SPF value after UV irradiation. Particularly, the SPF value may be increased by 3-80%, preferably 5-77%, as compared to the SPF value before UV irradiation. The cosmetic composition for UV protection according to the present disclosure shows an increased effect of protecting UV-A (320-400 nm) and UV-B (280-320 nm), and preferably shows a significantly increased effect of protecting UV-B, after UV irradiation.

The present disclosure also provides a method for preparing a cosmetic composition for UV protection according to the present disclosure, including a step of mixing a sunscreen having a methoxycinnamate structure with polar oil, wherein the sunscreen includes isoamyl p-methoxycinnamate, and the content of the polar oil is equal to or smaller than the content of isoamyl p-methoxycinnamate. The same as described above with reference to the cosmetic composition for UV protection according to the present disclosure may be applied to the method.

Advantageous Effects

The cosmetic composition for UV protection according to the present disclosure shows an increased UV protection efficiency upon the exposure to UV light, and particularly shows a significantly increased effect of protecting UV-A (320-400 nm) and UV-B (280-320 nm). In addition, the cosmetic composition for UV protection according to the present disclosure includes a specific content of hydrocarbon oil, and thus shows a significantly improved feeling of use.

BEST MODE

Hereinafter, the present disclosure will be explained in more detail with reference to exemplary embodiments. The present disclosure may, however, be embodied in many different forms and should not be construed as limited to the exemplary embodiments set forth therein. The following Examples are provided so that the present disclosure will be understood more fully by those skilled in the art

Test Example 1: UV Protection Effect Before and After UV Irradiation

Each of the five types of typical sunscreens as shown in the following Table 1 was applied to a PMMA plate (Helio-Screen Labs, HD6) at 1.3 mg/cm$^2$, and in-vitro SPF thereof was measured by using SPF-290S (Optometrics Corporation) before and after irradiating UV light at 2MED (minimum erythema dose) through a UV irradiating system (Solar Simulator 16S, Solar light company). Herein, in-vitro SPF was measured at six different portions of the PMMA plate, and the average value was recorded. The results are shown in Table 1.

TABLE 1

| UV filter | SPF (before UV irradiation) | SPF (after UV irradiation) | Change in SPF value | Change in SPF (%) |
|---|---|---|---|---|
| OMC | 15.84 ± 1.05 | 23.27 ± 3.07 | 7.43 | 46.91 |
| IMC | 18.19 ± 1.12 | 26.33 ± 2.3 | 8.14 | 44.75 |
| Ethylhexyl salicylate | 10.11 ± 161 | 10.10 ± 1.66 | −0.01 | −0.10 |
| Polysilicone 15 | 14.59 ± 0.41 | 14.65 ± 0.34 | 0.06 | −5.16 |
| Octocrylene | 27.11 ± 6.79 | 25.71 ± 10.69 | −1.40 | −5.16 |

* OMC: Ethylhexyl methoxycinnamate/IMC: Isoamyl p-methoxycinnamate

It can be seen from the above results that OMC or IMC having a methoxycinnamate structure shows a boost in in-vitro SPF value, while the remaining sunscreens show no significant change.

Test Example 2: UV Protection Effect Depending on Content of OMC and IMC

The cosmetic products for UV protection were obtained according to the composition of the following Table 2. Part A and Part B were prepared individually and warmed to 75° C. While Part B was introduced gradually to Part B, emulsification was carried out for 5 minutes by using a homomixer, followed by cooling to 30° C. Each of the resultant samples was determined in terms of SPF value before and after UV irradiation in the same manner as Test Example 1. The results are shown in the following Table 3.

TABLE 2

|   |   |   | Comp. Ex. 1 | Ex. 1 | Ex. 2 | Ex. 3 | Ex. 4 | Ex. 5 | Ex. 6 |
|---|---|---|---|---|---|---|---|---|---|
| A | 1 | Purified water | to 100 | to 100 | to 100 | to 100 | to 100 | to 100 | to 100 |
|   | 2 | Sodium polyacrylate | 0.5 | 0.5 | 0.5 | 0.5 | 0.5 | 0.5 | 0.5 |
| B | 3 | OMC | 0.5 | 1 | 1.5 | 2 | 2.5 | 5 | 7.5 |
|   | 4 | IMC | 0.5 | 1 | 1.5 | 2 | 2.5 | 5 | 7.5 |

* OMC: Ethylhexyl methoxycinnamate/IMC: Isoamyl p-methoxycinnamate

TABLE 3

|   | SPF (before UV irradiation) | SPF (after UV irradiation) | Change in SPF value | Change in SPF (%) |
|---|---|---|---|---|
| Comp. Ex. 1 | 2.18 ± 0.32 | 1.75 ± 0.24 | −0.43 | −19.72 |
| Ex. 1 | 2.7 ± 0.31 | 3.09 ± 0.22 | 0.39 | 14.44 |
| Ex. 2 | 3.93 ± 0.4 | 4.02 ± 0.53 | 0.09 | 2.29 |
| Ex. 3 | 4.46 ± 0.72 | 5.88 ± 0.63 | 1.42 | 31.84 |
| Ex. 4 | 6.31 ± 0.89 | 7.85 ± 0.89 | 1.54 | 24.41 |
| Ex. 5 | 6.62 ± 1.64 | 11.68 ± 1.45 | 5.06 | 76.44 |
| Ex. 6 | 7.66 ± 1.44 | 13.45 ± 1.44 | 5.79 | 75.59 |

Test Example 3: UV Protection Effect Depending on Content of Silicone Oil

The samples were prepared according to the composition of the following Table 4 in the same manner as described above. Each sample was determined in terms of in-vitro SPF before and after UV irradiation, and the in-vitro SPF values before and after UV irradiation were compared with each other. The results are shown in the following Table 5.

TABLE 4

|   |   | Comp. Ex. 2 | Comp. Ex. 3 | Comp. Ex. 4 | Comp. Ex. 5 |
|---|---|---|---|---|---|
| A | Purified water | to 100 | to 100 | to 100 | to 100 |
|   | Magnesium sulfate | 1.0 | 1.0 | 1.0 | 1.0 |
|   | DPG | 5.0 | 5.0 | 5.0 | 5.0 |
| B | OMC | 7.0 | 7.0 | 7.0 | 7.0 |
|   | IMC | 7.0 | 7.0 | 7.0 | 7.0 |
|   | D5 | 0.0 | 5 | 10 | 15 |
|   | BEMT | 1.0 | 1.0 | 1.0 | 1.0 |
|   | Abil EM 180 | 3.0 | 3.0 | 3.0 | 3.0 |
|   | TiO$_2$ | 2.0 | 2.0 | 2.0 | 2.0 |
|   | ZnO | 2.0 | 2.0 | 2.0 | 2.0 |

* OMC: Ethylhexyl methoxy cinnamate/IMC: Isoamyl p-methoxycinnamate/D5: Cyclopentasiloxane/BEMT: Bis-ethylhexyloxyphenol methoxyphenyl triazine/Abil EM 180: Cetyl PEG/PPG-10/1 Dimethicone

TABLE 5

|  | SPF (before UV irradiation) | SPF (after UV irradiation) | Change in SPF value | Change in SPF (%) |
|---|---|---|---|---|
| Comp. Ex. 2 | 28.74 ± 13.97 | 38.45 ± 23.03 | 9.71 | 33.79 |
| Comp. Ex. 3 | 30.77 ± 17.47 | 44.65 ± 27.46 | 13.88 | 45.11 |
| Comp. Ex. 4 | 30.68 ± 15.55 | 40.62 ± 23.05 | 9.94 | 32.40 |
| Comp. Ex. 5 | 37.67 ± 16.54 | 46.31 ± 24.51 | 8.64 | 22.94 |

The test was carried out to determine the effect of the present disclosure depending on the content of silicone oil. As can be seen from the test results of Comparative Examples 2-5, when the content of silicone oil is increased, the effect of the present disclosure is maintained. However, since silicone oil shows poor compatibility with OMC and IMC, each sample shows slightly reduced stability.

Test Example 4: UV Protection Effect Depending on Content of Hydrocarbon Oil

The samples were prepared according to the composition of the following Table 6 in the same manner as described above. Each sample was determined in terms of in-vitro SPF before and after UV irradiation, and the in-vitro SPF values before and after UV irradiation were compared with each other. The results are shown in the following Table 7.

TABLE 6

|  |  | Comp. Ex. 6 | Comp. Ex. 7 | Ex. 8 | Ex. 9 | Ex. 10 | Comp. Ex. 8 | Ex. 11 | Comp. Ex. 9 | Ex. 12 |
|---|---|---|---|---|---|---|---|---|---|---|
| A | Purified water | to 100 | to 100 | to 100 | to 100 | to 100 | to 100 | to 100 | to 100 | to 100 |
|  | Magnesium sulfate | 1.0 | 1.0 | 1.0 | 1.0 | 1.0 | 1.0 | 1.0 | 1.0 | 1.0 |
|  | DPG | 5.0 | 5.0 | 5.0 | 5.0 | 5.0 | 5.0 | 5.0 | 5.0 | 5.0 |
| B | OMC | 7.0 | 7.0 | 7.0 | 7.0 | 7.0 | 7.0 | 7.0 | 7.0 | 7.0 |
|  | IMC | 7.0 | 7.0 | 7.0 | 7.0 | 7.0 | 7.0 | 7.0 | 7.0 | 7.0 |
|  | Isododecane | 1.0 | 4.0 | 7.0 | 10.0 | 13.0 |  |  |  |  |
|  | Isohexadecane |  |  |  |  |  | 4.0 | 10.0 |  |  |
|  | Mineral oil |  |  |  |  |  |  |  | 4.0 | 10.0 |
|  | BEMT | 1.0 | 1.0 | 1.0 | 1.0 | 1.0 | 1.0 | 1.0 | 1.0 | 1.0 |
|  | Abil EM 180 | 1.5 | 1.5 | 1.5 | 1.5 | 1.5 | 1.5 | 1.5 | 1.5 | 1.5 |
|  | Olivem 900 | 3.0 | 3.0 | 3.0 | 3.0 | 3.0 | 3.0 | 3.0 | 3.0 | 3.0 |
|  | TiO$_2$ | 2.0 | 2.0 | 2.0 | 2.0 | 2.0 | 2.0 | 2.0 | 2.0 | 2.0 |
|  | ZnO | 2.0 | 2.0 | 2.0 | 2.0 | 2.0 | 2.0 | 2.0 | 2.0 | 2.0 |

* OMC: Ethylhexyl methoxycinnamate/IMC: Isoamyl p-methoxycinnamate/BEMT: Bis-ethylhexyloxyphenol methoxyphenyl triazine/Abil EM 180: Cetyl PEG/PPG-10/1 Dimethicone/Olivem 900: sorbitan olivate

TABLE 7

|  | SPF (before UV irradiation) | SPF (after UV irradiation) | Change in SPF value | Change in SPF (%) |
|---|---|---|---|---|
| Comp. Ex. 6 | 43.39 ± 3.91 | 57.52 ± 5.82 | 14.13 | 32.57 |
| Comp. Ex. 7 | 36.69 ± 7.03 | 47.81 ± 7.57 | 11.12 | 30.31 |
| Ex. 8 | 44.16 ± 7.53 | 58.43 ± 9.29 | 14.27 | 32.31 |
| Ex. 9 | 44.01 ± 7.35 | 56.9 ± 9.97 | 12.89 | 29.29 |
| Ex. 10 | 42.27 ± 5.46 | 50.61 ± 8.09 | 8.34 | 19.73 |
| Comp. Ex. 8 | 37.91 ± 7.18 | 46.66 ± 9.05 | 8.75 | 23.08 |
| Ex. 11 | 46.96 ± 9 | 56.4 ± 10.32 | 9.44 | 20.10 |
| Comp. Ex. 9 | 28.86 ± 6.35 | 37.51 ± 8.94 | 8.65 | 29.97 |
| Ex. 12 | 27.7 ± 3.04 | 37.36 ± 7.44 | 9.66 | 34.87 |

The test was carried out to determine the effect of the present disclosure depending on the type and content of hydrocarbon oil. As can be seen from the test results of Comparative Examples 6-9 and Examples 9-12, the effect of increasing SPF according to the present disclosure is realized sufficiently regardless of the type and content of hydrocarbon oil. However, in the case of Comparative Examples 6-9 having a content of hydrocarbon oil of less than 5%, each sample shows an excessively stiff feeling of use and thus cannot satisfy the fundamental quality standard of cosmetic products. In the case of Examples 9-12 having a content of hydrocarbon oil of 5% or more, the effect of increasing SPF is realized sufficiently, and each sample shows excellent skin applicability.

Figure 1:
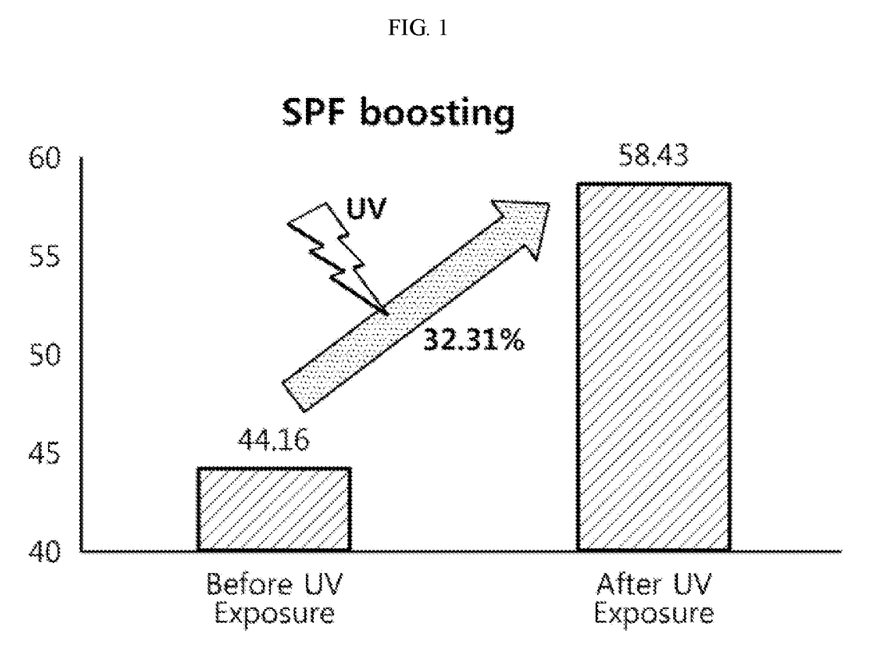
FIG. 1 shows the result of a boost in UV protection efficiency according to an embodiment (Example 8) of the present disclosure.
Figure 2:
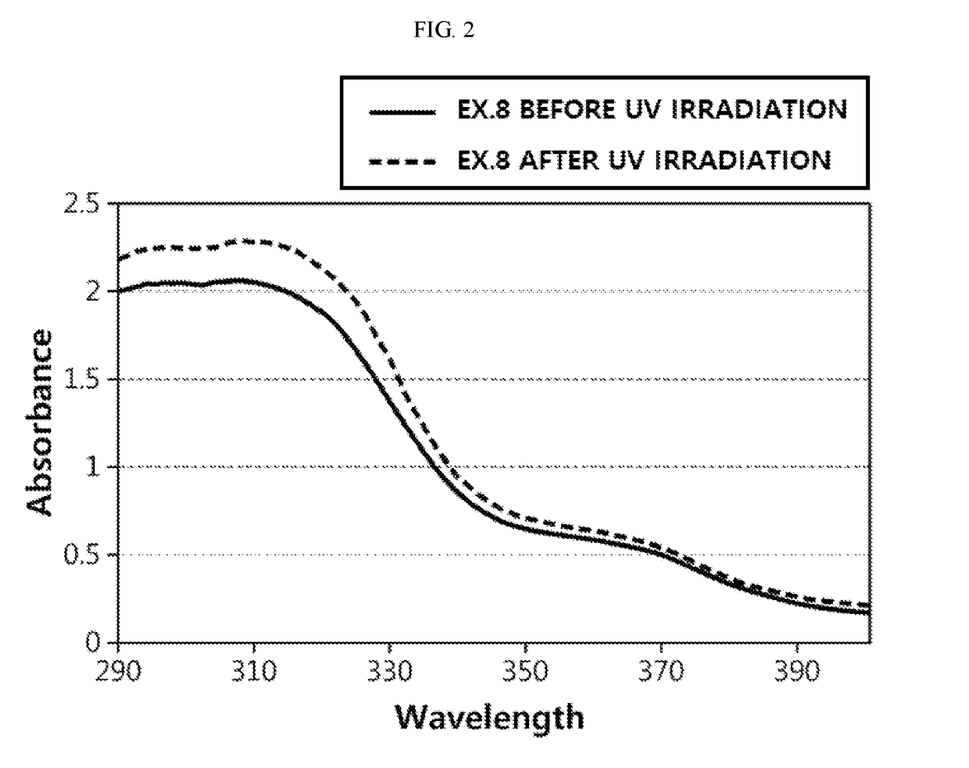
FIG. 2 shows the result of a change in absorbance according to an embodiment (Example 8) of the present disclosure, before and after UV irradiation.

FIG. 2 shows a change in absorbance in the UV region of Example 8 before and after UV irradiation. The data measured by using SPF-290S (Optometrics Corporation) are used as absorbance data to determine in-vitro SPF values. The absorbance of Example 8 before UV irradiation is represented by a solid line, while the absorbance of Example 8 after UV irradiation is represented by a dotted line. As shown in FIG. 2, Example 8 shows a boost in absorbance over the whole UV region after UV irradiation. Such a boost in SPF after UV irradiation is likely to be induced from a significant increase in absorbance in the UV-A (320-400 nm) and UV-B (280-320 nm) regions, particularly in the UV-B region.

Test Example 5: UV Protection Effect Depending on Content of Polar Oil

The samples were prepared according to the composition of the following Table 8 in the same manner as described above. Each sample was determined in terms of in-vitro SPF before and after UV irradiation, and the in-vitro SPF values before and after UV irradiation were compared with each other. The results are shown in the following Table 9.

TABLE 8

|   |   | Ex. 13 | Comp. Ex. 10 | Comp. Ex. 11 | Ex. 14 | Comp. Ex. 12 | Comp. Ex. 13 |
|---|---|---|---|---|---|---|---|
| A | Purified water | to 100 | to 100 | to 100 | to 100 | to 100 | to 100 |
|   | Magnesium sulfate | 1.0 | 1.0 | 1.0 | 1.0 | 1.0 | 1.0 |
|   | DPG | 5.0 | 5.0 | 5.0 | 5.0 | 5.0 | 5.0 |
| B | OMC | 7.0 | 7.0 | 7.0 | 7.0 | 7.0 | 7.0 |
|   | IMC | 7.0 | 7.0 | 7.0 | 7.0 | 7.0 | 7.0 |
|   | Cetylethyl hexanoate | 4.0 | 10.0 | 13.0 | — | — | — |
|   | Caprylic/capric Glycerides | — | — | — | 4.0 | 10.0 | 13.0 |
|   | BEMT | 1.0 | 1.0 | 1.0 | 1.0 | 1.0 | 1.0 |
|   | Abil EM 180 | 1.5 | 1.5 | 1.5 | 1.5 | 1.5 | 1.5 |
|   | Olivem 900 | 3.0 | 3.0 | 3.0 | 3.0 | 3.0 | 3.0 |
|   | $TiO_2$ | 2.0 | 2.0 | 2.0 | 2.0 | 2.0 | 2.0 |
|   | ZnO | 2.0 | 2.0 | 2.0 | 2.0 | 2.0 | 2.0 |

* OMC: Ethylhexyl methoxycinnamate/IMC: Isoamyl p-methoxycinnamate/BEMT: Bis-ethylhexyloxyphenol methoxyphenyl triazine/Abil EM 180: Cetyl PEG/PPG-10/1 Dimethicone/Olivem 900: Sorbitan olivate

TABLE 9

|   | SPF (before UV irradiation) | SPF (after UV irradiation) | Change in SPF value | Change in SPF (%) |
|---|---|---|---|---|
| Ex. 13 | 25.5 ± 4.38 | 33.62 ± 7.93 | 8.12 | 31.84 |
| Comp. Ex. 10 | 39.88 ± 8.01 | 39.98 ± 8.2 | 0.1 | 0.25 |
| Comp. Ex. 11 | 35.73 ± 3.25 | 35.62 ± 2.61 | −0.11 | −0.31 |
| Ex. 14 | 28.09 ± 4.85 | 36.99 ± 5.68 | 8.9 | 31.68 |
| Comp. Ex. 12 | 42.59 ± 2.1 | 42.44 ± 2.1 | −0.15 | −0.35 |
| Comp. Ex. 13 | 40.99 ± 4.81 | 41.29 ± 4.4 | 0.3 | 0.73 |

The test was carried out to determine the effect of the present disclosure depending on the type and content of polar oil. When the content of polar oil is 5% or less, the UV protection effect is increased significantly, as can be seen from the results of Examples 13 and 14. However, when the content of polar oil is larger than 5%, it is not possible to realize a boost in UV protection efficiency, as can be seen from the results of Comparative Examples 10-13.

Figure 3:
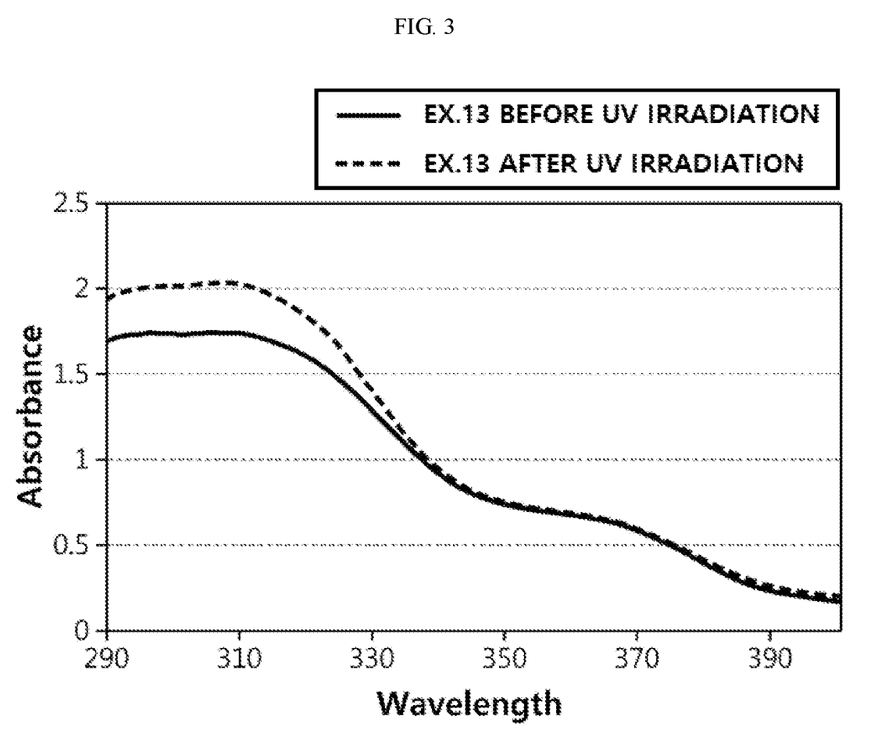
FIG. 3 shows the result of a change in absorbance according to an embodiment (Example 13) of the present disclosure, before and after UV irradiation.

FIG. 3 shows a graph illustrating the absorbance of Example 13 before and after UV irradiation. Referring to the graph of absorbance, it can be seen that UV protection efficiency is increased in the whole UV region.

Figure 4:
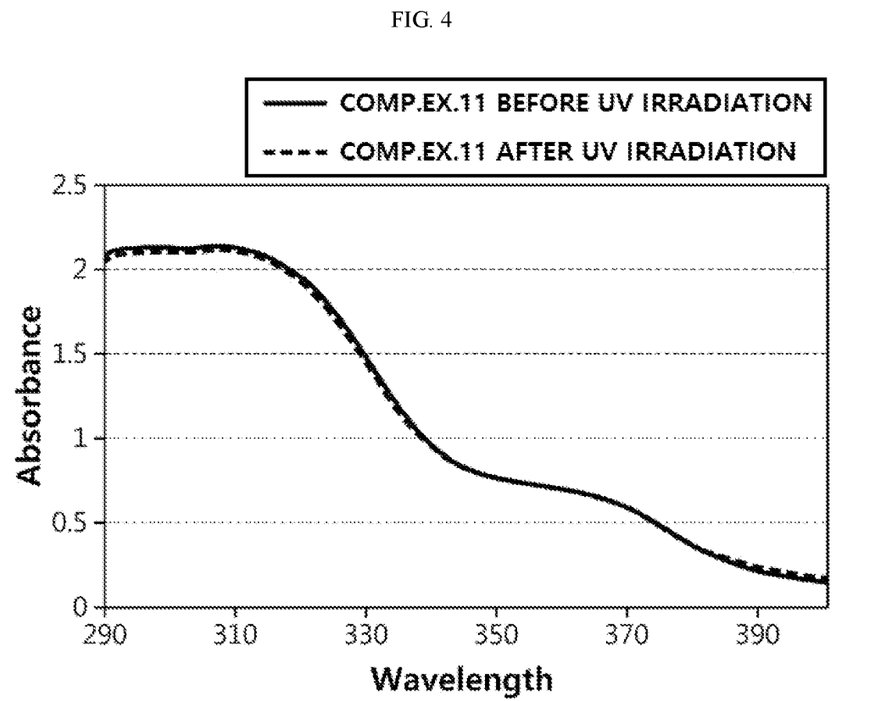
FIG. 4 shows the result of a change in absorbance according to Comparative Example 11, before and after UV irradiation.

FIG. 4 shows a graph illustrating the absorbance of Comparative Example 11 before and after UV irradiation. Referring to FIG. 4 showing a change in absorbance of Comparative Example 11, it can be seen that there is little change in absorbance, and Example 11 rather shows a slight decrease in absorbance in the UVB region.

Test Example 6: UV Protection Effect Depending on Type and Content of Polar Oil

The samples were prepared according to the composition of the following Table 10 in the same manner as described above. Each sample was determined in terms of in-vitro SPF before and after UV irradiation, and the in-vitro SPF values before and after UV irradiation were compared with each other. The results are shown in the following Table 11.

TABLE 10

|   |   | Ex. 15 | Comp. Ex. 14 | Ex. 16 | Comp. Ex. 15 | Ex. 17 | Comp. Ex. 16 | Ex. 18 | Comp. Ex. 17 | Ex. 19 | Comp. Ex. 18 |
|---|---|---|---|---|---|---|---|---|---|---|---|
| A | Purified water | To 100 | To 100 | To 100 | To 100 | To 100 | To 100 | To 100 | To 100 | To 100 | To 100 |
|   | Magnesium sulfate | 1.0 | 1.0 | 1.0 | 1.0 | 1.0 | 1.0 | 1.0 | 1.0 | 1.0 | 1.0 |
|   | DPG | 5.0 | 5.0 | 5.0 | 5.0 | 5.0 | 5.0 | 5.0 | 5.0 | 5.0 | 5.0 |
| B | OMC | 7.0 | 7.0 | 7.0 | 7.0 | 7.0 | 7.0 | 7.0 | 7.0 | 7.0 | 7.0 |
|   | IMC | 7.0 | 7.0 | 7.0 | 7.0 | 7.0 | 7.0 | 7.0 | 7.0 | 7.0 | 7.0 |
|   | Isododecane | 7.0 | 7.0 | 7.0 | 7.0 | 7.0 | 7.0 | 7.0 | 7.0 | 7.0 | 7.0 |
|   | Caprylic/capric glycerides | 3.0 | 9.0 | — | — | — | — | — | — | — | — |
|   | Phenethyl benzoate | — | — | 3.0 | 9.0 | — | — | — | — | — | — |
|   | Dicaprylyl carbonate | — | — | — | — | 3.0 | 9.0 | — | — | — | — |
|   | C12-15 Alkyl benzoate | — | — | — | — | — | — | 3.0 | 9.0 | — | — |
|   | Octocrylene | — | — | — | — | — | — | — | — | 3.0 | 9.0 |
|   | BEMT | 1.0 | 1.0 | 1.0 | 1.0 | 1.0 | 1.0 | 1.0 | 1.0 | 1.0 | 1.0 |
|   | Abil EM 180 | 1.5 | 1.5 | 1.5 | 1.5 | 1.5 | 1.5 | 1.5 | 1.5 | 1.5 | 1.5 |
|   | Olivem 900 | 3.0 | 3.0 | 3.0 | 3.0 | 3.0 | 3.0 | 3.0 | 3.0 | 3.0 | 3.0 |
|   | $TiO_2$ | 2.0 | 2.0 | 2.0 | 2.0 | 2.0 | 2.0 | 2.0 | 2.0 | 2.0 | 2.0 |
|   | ZnO | 2.0 | 2.0 | 2.0 | 2.0 | 2.0 | 2.0 | 2.0 | 2.0 | 2.0 | 2.0 |

* OMC: Ethylhexyl methoxycinnamate/IMC: Isoamyl p-methoxycinnamate/BEMT: Bis-ethylhexyloxyphenol methoxyphenyl triazine/Abil EM 180: Cetyl PEG/PPG-10/1 Dimethicone/Olivem 900: Sorbitan olivate

TABLE 11

| | SPF (before UV irradiation) | SPF (after UV irradiation) | Change in SPF value | Change in SPF (%) |
|---|---|---|---|---|
| Ex. 15 | 24.54 ± 1.35 | 25.98 ± 1.52 | 1.44 | 5.87 |
| Comp. Ex. 14 | 25.26 ± 2.76 | 24.87 ± 2.87 | −0.39 | −1.54 |
| Ex. 16 | 37.55 ± 2.85 | 40.89 ± 2.7 | 3.34 | 8.89 |
| Comp. Ex. 15 | 26.38 ± 7.63 | 24.24 ± 1.76 | −2.14 | −8.11 |
| Ex. 17 | 28.31 ± 1.61 | 28.89 ± 1.74 | 0.58 | 2.05 |
| Comp. Ex. 16 | 23.63 ± 1.96 | 23.5 ± 2.71 | −0.13 | −0.55 |
| Ex. 18 | 28.87 ± 1.79 | 29.24 ± 1.89 | 0.37 | 1.28 |
| Comp. Ex. 17 | 24.77 ± 1.55 | 23.37 ± 0.94 | −1.40 | −5.65 |
| Ex. 19 | 25.33 ± 6.61 | 36.69 ± 5.54 | 11.36 | 44.85 |
| Comp. Ex. 18 | 47.82 ± 5.46 | 46.86 ± 4.58 | −0.96 | −2.01 |

The test was carried out to further determine the effect of the present disclosure depending on the type and content of polar oil. When the content of polar oil is 5% or less, the UV protection effect is increased significantly, as can be seen from the results of Examples 15-19. However, when the content of polar oil is larger than 5%, it is not possible to realize a boost in UV protection efficiency, as can be seen from the results of Comparative Examples 14-18.

Test Example 7: UV Protection Effect Depending on Type of Oil in O/W Formulation The cosmetic products for UV protection were obtained according to the composition of the following Table 12 as follows. The ingredients of Part A were mixed thoroughly at 75° C. Ingredient 11 was introduced to Ingredient 10 and dispersed therein for 30 minutes by using Disper. The remaining ingredients of Part B were introduced thereto and the resultant mixture warmed to 75° C. While Part A was introduced gradually to Part B, emulsification was carried out for 10 minutes by using a homo-mixer, followed by cooling to 30° C.

Each sample was determined in terms of SPF value before and after UV irradiation in the same manner as Test Example 1. The results are shown in the following Table 13.

TABLE 13

| | SPF (before UV irradiation) | SPF (after UV irradiation) | Change in SPF value | Change in SPF (%) |
|---|---|---|---|---|
| Ex. 20 | 14.46 ± 2.21 | 20.84 ± 3.53 | 6.38 | 44.12 |
| Comp. Ex. 19 | 8.02 ± 1.43 | 7.15 ± 1.38 | −0.87 | −10.85 |
| Comp. Ex. 20 | 12.07 ± 2 | 11.07 ± 2.01 | −1.00 | −8.29 |
| Ex. 21 | 8.39 ± 0.11 | 14.83 ± 1.59 | 6.44 | 76.76 |
| Ex. 22 | 18.1 ± 2.96 | 27.71 ± 4.85 | 9.61 | 53.09 |
| Ex. 23 | 17.61 ± 1.91 | 22.58 ± 2.1 | 4.97 | 28.22 |

Example 20 including no oil or Examples 21-23 including nonpolar oil show a boost in in-vitro SPF value by UV light. However, Comparative Examples 19 and 20 including 10 wt % of polar oil shows a decrease in in-vitro SPF value by UV light. It can be seen from the above results that it is required to limit the content of polar oil, unlike nonpolar oil, so that the cosmetic composition for UV protection according to the present disclosure may realize an excellent UV protection effect.

Test Example 8: UV Protection Effect of OMC and IMC Depending on Oil in

O/W Formulation

The cosmetic products for UV protection were prepared according to the compositions of the following Table 14 and Table 15 as follows. The ingredients of Part A were mixed thoroughly at 75° C. Ingredient 7 was introduced to Ingredient 6 and dispersed therein for 30 minutes by using Disper. The remaining ingredients of Part B were introduced thereto and the resultant mixture warmed to 75° C. While Part A was introduced gradually to Part B, emulsification was carried out for 10 minutes by using a homo-mixer, followed by cooling to 30° C.

TABLE 12

| | | | Ex. 20 | Comp. Ex. 19 | Comp. Ex. 20 | Ex. 21 | Ex. 22 | Ex. 23 |
|---|---|---|---|---|---|---|---|---|
| A | 1 | OMC | 5.0 | 5.0 | 5.0 | 5.0 | 5.0 | 5.0 |
| | 2 | IMC | 5.0 | 5.0 | 5.0 | 5.0 | 5.0 | 5.0 |
| | 3 | BEMT | 1.0 | 1.0 | 1.0 | 1.0 | 1.0 | 1.0 |
| | 4 | Hydrogenated lecithin | 1.5 | 1.5 | 1.5 | 1.5 | 1.5 | 1.5 |
| | 5 | Cetylethyl hexanoate | — | 10.0 | — | — | — | — |
| | 6 | Caprylic/capric glycerides | — | — | 10.0 | — | — | — |
| | 7 | Isododecane | — | — | — | 10.0 | — | — |
| | 8 | Dimethicone | — | — | — | — | 10.0 | — |
| | 9 | Cyclopentasiloxane | — | — | — | — | — | 10.0 |
| B | 10 | Water | to 100 | to 100 | to 100 | to 100 | to 100 | to 100 |
| | 11 | Sodium polyacrylate | 0.5 | 0.5 | 0.5 | 0.5 | 0.5 | 0.5 |
| | 12 | Dexpanthenol | 1.0 | 1.0 | 1.0 | 1.0 | 1.0 | 1.0 |
| | 13 | 1,2-Hexanediol | 2.0 | 2.0 | 2.0 | 2.0 | 2.0 | 2.0 |

\* OMC: Ethylhexyl methoxycinnamate/IMC: Isoamyl p-methoxycinnamate/BEMT: Bis-ethylhexyloxyphenol methoxyphenyl triazine

TABLE 14

|   |   |                      | Ex. 24 | Comp. Ex. 21 | Comp. Ex. 22 | Comp. Ex. 23 | Ex. 25 | Ex. 26 | Ex. 27 | Ex. 28 | Ex. 29 | Ex. 30 |
|---|---|----------------------|--------|--------------|--------------|--------------|--------|--------|--------|--------|--------|--------|
| A | 1 | OMC                  | 7.00   | 7.00         | 7.00         | 7.00         | 7.00   | 7.00   | 7.00   | 7.00   | 7.00   | 7.00   |
|   | 2 | Cetylethyl hexanoate | —      | 1.00         | 4.00         | 7.00         | —      | —      | —      | —      | —      | —      |
|   | 3 | Cyclopentasiloxane   | —      | —            | —            | —            | 1.00   | 4.00   | 7.00   | —      | —      | —      |
|   | 4 | dimethicone          | —      | —            | —            | —            | —      | —      | —      | 1.00   | 4.00   | 7.00   |
|   | 5 | BEMT                 | 1.00   | 1.00         | 1.00         | 1.00         | 1.00   | 1.00   | 1.00   | 1.00   | 1.00   | 1.00   |
|   | 6 | hydrogenated lecithin| 1.50   | 1.50         | 1.50         | 1.50         | 1.50   | 1.50   | 1.50   | 1.50   | 1.50   | 1.50   |
| B | 7 | Purified water       | to 100 | to 100       | to 100       | to 100       | to 100 | to 100 | to 100 | to 100 | to 100 | to 100 |
|   | 8 | sodium polyacrylate  | 0.50   | 0.50         | 0.50         | 0.50         | 0.50   | 0.50   | 0.50   | 0.50   | 0.50   | 0.50   |
|   | 9 | 1,2-Hexanediol       | 2.00   | 2.00         | 2.00         | 2.00         | 2.00   | 2.00   | 2.00   | 2.00   | 2.00   | 2.00   |

\* OMC: Ethylhexyl methoxycinnamate/IMC: Isoamyl p-methoxycinnamate/CEH: Cetylethyl hexanoate/BEMT: Bis-ethylhexyloxyphenol methoxyphenyl triazine

TABLE 15

|   |   |                       | Ex. 31 | Ex. 32 | Ex. 33 | Ex. 34 | Ex. 35 | Ex. 36 | Ex. 37 | Ex. 38 | Ex. 39 | Ex. 40 |
|---|---|-----------------------|--------|--------|--------|--------|--------|--------|--------|--------|--------|--------|
| A | 1 | IMC                   | 7.00   | 7.00   | 7.00   | 7.00   | 7.00   | 7.00   | 7.00   | 7.00   | 7.00   | 7.00   |
|   | 2 | Cetylethyl hexanoate  | —      | 1.00   | 4.00   | 7.00   | —      | —      | —      | —      | —      | —      |
|   | 3 | cyclopentasiloxane    | —      | —      | —      | —      | 1.00   | 4.00   | 7.00   | —      | —      | —      |
|   | 4 | dimethicone           | —      | —      | —      | —      | —      | —      | —      | 1.00   | 4.00   | 7.00   |
|   | 5 | BEMT                  | 1.00   | 1.00   | 1.00   | 1.00   | 1.00   | 1.00   | 1.00   | 1.00   | 1.00   | 1.00   |
|   | 6 | hydrogenated lecithin | 1.50   | 1.50   | 1.50   | 1.50   | 1.50   | 1.50   | 1.50   | 1.50   | 1.50   | 1.50   |
| B | 7 | Purified water        | to 100 | to 100 | to 100 | to 100 | to 100 | to 100 | to 100 | to 100 | to 100 | to 100 |
|   | 8 | sodium polyacrylate   | 0.50   | 0.50   | 0.50   | 0.50   | 0.50   | 0.50   | 0.50   | 0.50   | 0.50   | 0.50   |
|   | 9 | 1,2-Hexanediol        | 2.00   | 2.00   | 2.00   | 2.00   | 2.00   | 2.00   | 2.00   | 2.00   | 2.00   | 2.00   |

\* OMC: Ethylhexyl methoxycinnamate/IMC: Isoamyl p-methoxycinnamate/CEH: Cetylethyl hexanoate/BEMT: Bis-ethylhexyloxyphenol methoxyphenyl triazine Each sample was applied to a PMMA plate (HelioScreen Labs, HD6) at 1.3 mg/cm², and in-vitro SPF thereof was measured before and after irradiating UV light with a wavelength of 321 nm at 2MED by using a laboratory UV irradiation system, bio-sun (Vilber Lourmat). The results are shown in the following Table 16 and Table 17. Herein, in-vitro SPF was calculated according to the following formula by using the absorbance measured through a spectrophotometer (Epoch). The absorbance was measured at nine different points on the PMMA plate, and the average of the SPF values calculated from the absorbance values was used.

$$SPF = \sum_{290}^{400} E_\lambda S_\lambda \bigg/ \sum_{290}^{400} E_\lambda S_\lambda T_\lambda$$

E: Erythemal action spectrum
$S_\lambda$: Spectral irradiance (W/m²/nm)
$T_\lambda$: Transmittance

TABLE 16

|              | SPF (before UV irradiation) | SPF (after UV irradiation) | Change in SPF value | Change in SPF (%) |
|--------------|-----------------------------|----------------------------|---------------------|-------------------|
| Ex. 24       | 6.08 ± 0.86                 | 7.1 ± 1.17                 | 1.02                | 16.78             |
| Comp. Ex. 21 | 6.9 ± 1.03                  | 6.34 ± 1.02                | −0.56               | −8.12             |
| Comp. Ex. 22 | 4.98 ± 0.26                 | 4.22 ± 0.22                | −0.76               | −15.26            |
| Comp. Ex. 23 | 6.15 ± 0.83                 | 5.2 ± 0.6                  | −0.95               | −15.45            |
| Ex. 25       | 7.66 ± 0.84                 | 7.86 ± 1.00                | 0.20                | 2.61              |
| Ex. 26       | 8.06 ± 0.59                 | 8.44 ± 0.6                 | 0.38                | 4.71              |
| Ex. 27       | 7.25 ± 0.59                 | 7.62 ± 0.57                | 0.37                | 5.10              |
| Ex. 28       | 6.76 ± 0.74                 | 7.36 ± 0.93                | 0.60                | 8.88              |
| Ex. 29       | 6.84 ± 0.78                 | 7.33 ± 0.89                | 0.49                | 7.16              |
| Ex. 30       | 4.73 ± 0.73                 | 5.74 ± 0.93                | 1.01                | 21.35             |

TABLE 17

|         | SPF (before UV irradiation) | SPF (after UV irradiation) | Change in SPF value | Change in SPF (%) |
|---------|-----------------------------|----------------------------|---------------------|-------------------|
| Ex. 31  | 22.09 ± 2.26                | 23.79 ± 2.57               | 1.70                | 7.70              |
| Ex. 32  | 21.79 ± 0.96                | 24.95 ± 1.02               | 3.16                | 14.50             |
| Ex. 33  | 11.12 ± 1.23                | 12.18 ± 1.41               | 1.06                | 9.53              |
| Ex. 34  | 8.46 ± 1.88                 | 8.12 ± 2.04                | −0.34               | −4.02             |
| Ex. 35  | 22.29 ± 3.24                | 23.64 ± 3.25               | 1.35                | 6.06              |

TABLE 17-continued

|  | SPF (before UV irradiation) | SPF (after UV irradiation) | Change in SPF value | Change in SPF (%) |
|---|---|---|---|---|
| Ex. 36 | 20.07 ± 2.18 | 21.35 ± 2.36 | 1.28 | 6.38 |
| Ex. 37 | 21.38 ± 2.67 | 22.07 ± 2.53 | 0.69 | 3.23 |
| Ex. 3 8 | 23.37 ± 1.89 | 26.49 ± 2.15 | 3.12 | 13.35 |
| Ex. 39 | 22.05 ± 2.46 | 25.13 ± 2.74 | 3.08 | 13.97 |
| Ex. 40 | 24.41 ± 2.91 | 27.47 ± 3.01 | 3.06 | 12.54 |

In the case of Comparative Examples 21-23 using OMC alone, SPF is decreased after UV irradiation, even when a small amount of polar oil is present, and thus it is not possible to realize the effect of the present disclosure. In the case of Examples 25-30 including nonpolar oil in addition to OMC, it can be seen that UV protection efficiency is increased. In the case of Examples 32-34 using IMC alone, the negative effect of polar oil is reduced significantly. In the case of Examples 35-40 including nonpolar oil in addition to IMC, it can be seen that UV protection efficiency is increased.

Test Example 9: UV Protection Effect Depending on IMC and Polar Oil in O/W Formulation The cosmetic products for UV protection were prepared according to the compositions of the following Table 18 and Table 19 as follows. The ingredients of Part A were mixed thoroughly at 75° C. Ingredient 7 was introduced to Ingredient 6 and dispersed therein for 30 minutes by using Disper. Then, Ingredient 8 was introduced thereto and the resultant mixture warmed to 75° C. While Part A was introduced gradually to Part B, emulsification was carried out for 10 minutes by using a homo-mixer, followed by cooling to 30° C.

Each sample was applied to a PMMA plate (HelioScreen Labs, HD6) at 1.3 mg/cm$^2$, and in-vitro SPF thereof was measured before and after irradiating UV light at 2MED by using suntest XLS+ (solar simulator). The results are shown in the following Table 20. Herein, in-vitro SPF was calculated according to the following formula by using the absorbance measured through a spectrophotometer (Epoch). The absorbance was measured at nine different points on the PMMA plate, and the average of the SPF values calculated from the absorbance values was used.

$$SPF = \sum_{290}^{400} E_\lambda S_\lambda \bigg/ \sum_{290}^{400} E_\lambda S_\lambda T_\lambda$$

E: Erythemal action spectrum
$S_\lambda$: Spectral irradiance (W/m$^2$/nm)
$T_\lambda$: Transmittance

TABLE 20

|  | SPF (before UV irradiation) | SPF (after UV irradiation) | Change in SPF value | Change in SPF (%) |
|---|---|---|---|---|
| Comp. Ex. 24 | 4 67 ± 0.44 | 4.33 ± 0.49 | −0.34 | −7.27 |
| Comp. Ex. 25 | 4.91 ± 0.53 | 4.7 ± 0.35 | −0.22 | −4.42 |
| Comp. Ex. 26 | 5.87 ± 1.09 | 5.04 ± 0.94 | −0.82 | −14.06 |
| Comp. Ex. 27 | 6.15 ± 0.45 | 5.37 ± 0.76 | −0.79 | −12.79 |
| Ex. 41 | 6.37 ± 0.68 | 10.13 ± 1.8 | 3.76 | 58.99 |
| Comp. Ex. 28 | 6.18 ± 0.53 | 6.31 ± 0.69 | 0.13 | 2.15 |

TABLE 18

|  |  |  | Comp. Ex. 24 | Comp. Ex. 25 | Comp. Ex. 26 | Comp. Ex. 27 | Ex. 41 | Comp. Ex. 28 | Comp. Ex. 29 | Comp. Ex. 30 |
|---|---|---|---|---|---|---|---|---|---|---|
| A | 1 | OMC | 7.00 | 7.00 | 7.00 | 7.00 | 7.00 | 7.00 | 7.00 | 7.00 |
|  | 2 | IMC | 3.00 | 3.00 | 3.00 | 3.00 | 5.00 | 5.00 | 5.00 | 5.00 |
|  | 3 | CEH | 5.00 | 7.00 | 9.00 | 11.00 | 5.00 | 7.00 | 9.00 | 11.00 |
|  | 4 | BEMT | 1.00 | 1.00 | 1.00 | 1.00 | 1.00 | 1.00 | 1.00 | 1.00 |
|  | 5 | Hydrogenated lecithin | 1.50 | 1.50 | 1.50 | 1.50 | 1.50 | 1.50 | 1.50 | 1.50 |
| B | 6 | Purified water | to 100 | to 100 | to 100 | to 100 | to 100 | to 100 | to 100 | to 100 |
|  | 7 | Sodium polyacrylate | 0.50 | 0.50 | 0.50 | 0.50 | 0.50 | 0.50 | 0.50 | 0.50 |
|  | 8 | 1,2-Hexanediol | 2.00 | 2.00 | 2.00 | 2.00 | 2.00 | 2.00 | 2.00 | 2.00 |

* OMC: Ethylhexyl methoxycinnamate/IMC: Isoamyl p-methoxycinnamate/CEH: Cetylethyl hexanoate/BEMT: Bis-ethylhexyloxyphenol methoxyphenyl triazine

TABLE 19

|  |  |  | Ex. 42 | Ex. 43 | Comp. Ex. 31 | Comp. Ex. 32 | Ex. 44 | Ex. 45 | Ex. 46 | Comp. Ex. 33 |
|---|---|---|---|---|---|---|---|---|---|---|
| A | 1 | OMC | 7.00 | 7.00 | 7.00 | 7.00 | 7.00 | 7.00 | 7.00 | 7.00 |
|  | 2 | IMC | 7.00 | 7.00 | 7.00 | 7.00 | 9.00 | 9.00 | 9.00 | 9.00 |
|  | 3 | CEH | 5.00 | 7.00 | 9.00 | 11.00 | 5.00 | 7.00 | 9.00 | 11.00 |
|  | 4 | BEMT | 1.00 | 1.00 | 1.00 | 1.00 | 1.00 | 1.00 | 1.00 | 1.00 |
|  | 5 | Hydrogenated lecithin | 1.50 | 1.50 | 1.50 | 1.50 | 1.50 | 1.50 | 1.50 | 1.50 |
| B | 6 | Purified water | to 100 | to 100 | to 100 | to 100 | to 100 | to 100 | to 100 | to 100 |
|  | 7 | Sodium polyacrylate | 0.50 | 0.50 | 0.50 | 0.50 | 0.50 | 0.50 | 0.50 | 0.50 |
|  | 8 | 1,2-Hexanediol | 2.00 | 2.00 | 2.00 | 2.00 | 2.00 | 2.00 | 2.00 | 2.00 |

* OMC: Ethylhexyl methoxycinnamate/IMC: Isoamyl p-methoxycinnamate/CEH: Cetylethyl hexanoate/BEMT: Bis-ethylhexyloxyphenol methoxyphenyl triazine TABLE 20-continued

|  | SPF (before UV irradiation) | SPF (after UV irradiation) | Change in SPF value | Change in SPF (%) |
|---|---|---|---|---|
| Comp. Ex. 29 | 9.11 ± 2.59 | 8.25 ± 2.42 | −0.86 | −9.42 |
| Comp. Ex. 30 | 8.06 ± 1.88 | 6.39 ± 1.58 | −1.67 | −20.73 |
| Ex. 42 | 12.04 ± 1.76 | 21.34 ± 2.33 | 9.3 | 77.24 |
| Ex. 43 | 11.02 ± 1.63 | 14.97 ± 2.99 | 3.95 | 35.83 |
| Comp. Ex. 31 | 9.24 ± 2.25 | 8.66 ± 1.6 | −0.58 | −6.24 |
| Comp. Ex. 32 | 20.41 ± 4.59 | 18.76 ± 3.98 | −1.65 | −8.07 |
| Ex. 44 | 18.28 ± 1.4 | 25.26 ± 1.48 | 6.98 | 38.17 |
| Ex. 45 | 26.04 ± 3.7 | 29.1 ± 3.51 | 3.05 | 11.73 |
| Ex. 46 | 11.54 ± 2.07 | 14.75 ± 3.29 | 3.22 | 27.89 |
| Comp. Ex. 33 | 19.28 ± 2.53 | 19.67 ± 3.11 | 0.4 | 2.05 |

When the content of polar oil is equal to or small than the content of IMC, like Examples 41-46, in-vitro SPF values are increased by UV light. On the contrary, when the content of polar oil is larger than the content of IMC, like Comparative Examples 24-33, in-vitro SPF values are reduced or show a significantly reduced change. Therefore, it can be seen that the content of polar oil should be equal to or smaller than the content of a sunscreen, particularly IMC, so that the cosmetic composition for UV protection according to the present disclosure may realize an excellent UV protection effect.

Test Example 10: UV Protection Effect Depending on Content of Nonpolar Oil

The cosmetic products for UV protection were obtained according to the composition of the following Table 21. Part A and Part B were prepared individually and warmed to 75° C. While Part B was introduced gradually to Part B, emulsification was carried out for 5 minutes by using a homo-mixer, followed by cooling to 30° C. Each of the resultant samples was determined in terms of SPF value before and after UV irradiation in the same manner as Test Example 1. The results are shown in the following Table 22.

TABLE 21

|  |  |  | Ex. 47 | Ex. 48 | Ex. 49 | Ex. 50 |
|---|---|---|---|---|---|---|
| A | 1 | OMC | 5.00 | 5.00 | 5.00 | 5.00 |
|  | 2 | IMC | 5.00 | 5.00 | 5.00 | 5.00 |
|  | 3 | BEMT | 1.00 | 1.00 | 1.00 | 1.00 |
|  | 4 | hydrogenated lecithin | 1.50 | 1.50 | 1.50 | 1.50 |
|  | 5 | dimethicone | 5.00 | 10.00 | 15.00 | 20.00 |
| B | 6 | Purified water | to 100 | to 100 | to 100 | to 100 |
|  | 7 | sodium polyacrylate | 2.00 | 2.00 | 2.00 | 2.00 |
|  | 8 | 1,2-Hexanediol | 0.50 | 0.50 | 0.50 | 0.50 |

* OMC: Ethylhexyl methoxycinnamate/IMC: Isoamyl p-methoxycinnamate/CEH: Cetylethyl hexanoate/BEMT: Bis-ethylhexyloxyphenol methoxyphenyl triazine

TABLE 22

|  | SPF (before UV irradiation) | SPF (after UV irradiation) | Change in SPF value | Change in SPF (%) |
|---|---|---|---|---|
| Ex. 47 | 21.39 ± 1.53 | 24.05 ± 2.65 | 2.66 | 12.44 |
| Ex. 48 | 18.1 ± 2.96 | 27.71 ± 4.85 | 9.61 | 53.09 |
| Ex. 49 | 20.31 ± 2.34 | 28.94 ± 3.33 | 8.63 | 42.49 |
| Ex. 50 | 18.12 ± 2.64 | 29.24 ± 4.71 | 11.12 | 61.37 |

It can be seen that even when nonpolar oil is used up to 20%, like Examples 40-50, UV protection efficiency is increased by UV light.

Test Example 11: UV Protection Effect Depending on Content of OMC and IMC

The cosmetic products for UV protection were obtained according to the composition of the following Table 23. Part A and Part B were prepared individually and warmed to 75° C. While Part B was introduced gradually to Part B, emulsification was carried out for 5 minutes by using a homo-mixer, followed by cooling to 30° C. Each of the resultant samples was determined in terms of SPF value before and after UV irradiation in the same manner as Test Example 1. The results are shown in the following Table 24.

TABLE 23

|  |  |  | Ex. 51 | Ex. 52 | Ex. 53 | Comp. Ex. 34 | Comp. Ex. 35 |
|---|---|---|---|---|---|---|---|
| A | 1 | OMC | 5.00 | 5.00 | 5.00 | 5.00 | 5.00 |
|  | 2 | IMC | 5.00 | 5.00 | 5.00 | 5.00 | 5.00 |
|  | 3 | BEMT | 1.00 | 1.00 | 1.00 | 1.00 | 1.00 |
|  | 4 | hydrogenated lecithin | 1.50 | 1.50 | 1.50 | 1.50 | 1.50 |
|  | 5 | dimethicone | 10.00 | 7.50 | 5.00 | 2.50 | — |
|  | 6 | caprylic/Capric Glycerides | — | 2.50 | 5.00 | 7.50 | 10.00 |
| B | 7 | Purified water | to 100 | to 100 | to 100 | to 100 | to 100 |
|  | 8 | sodium polyacrylate | 2.00 | 2.00 | 2.00 | 2.00 | 2.00 |
|  | 9 | 1,2-Hexanediol | 0.50 | 0.50 | 0.50 | 0.50 | 0.50 |

* OMC: Ethylhexyl methoxycinnamate/IMC: Isoamyl p-methoxycinnamate/CEH: Cetylethyl hexanoate/BEMT: Bis-ethylhexyloxyphenol methoxyphenyl triazine

TABLE 24

|  | SPF (before UV irradiation) | SPF (after UV irradiation) | Change in SPF value | Change in SPF (%) |
|---|---|---|---|---|
| Ex. 51 | 18.1 ± 2.96 | 27.71 ± 4.85 | 9.61 | 53.09 |
| Ex. 52 | 7.6 ± 1.26 | 1.26 ± 9.75 | 2.15 | 28.29 |
| Ex. 53 | 7.11 ± 0.9 | 0.9 ± 8.28 | 1.17 | 16.46 |
| Comp. Ex. 34 | 4.84 ± 0.37 | 0.37 ± 4.55 | (0.29) | −5.99 |
| Comp. Ex. 35 | 12.07 ± 2 | 11.07 ± 2.01 | −1.00 | −8.29 |

It can be seen that when the content of polar oil is smaller than the content of IMC, like Examples 51-53, the effect of the present disclosure is maintained. On the contrary, it can be seen that when the content of polar oil is larger than the content of IMC, like Comparative Examples 34 and 35, it is not possible to realize the effect of the present disclosure.

Test Example 12: UV Protection Effect Depending on Emulsifier

The cosmetic products for UV protection were obtained according to the composition of the following Table 25 and Table 26. Part A and Part B were prepared individually and warmed to 75° C. While Part B was introduced gradually to Part B, emulsification was carried out for 5 minutes by using a homo-mixer, followed by cooling to 30° C. Each of the resultant samples was determined in terms of SPF value before and after UV irradiation in the same manner as Test Example 1. The results are shown in the following Table 27.

TABLE 25

| | | | |
|---|---|---|---|
| A | 1 | OMC | 7.00 |
| | 2 | IMC | 9.00 |
| | 3 | BEMT | 2.00 |
| | 4 | MT-100TV | 2.00 |
| | 5 | Emulsifier | 3.00 |
| B | 6 | Purified water | to 100 |
| | 7 | 1,2-Hexanediol | 2.00 |

TABLE 26

| | Emulsifier | Content |
|---|---|---|
| Ex. 54 | Lipomulse 165 | 3 |
| Ex. 55 | Olivem 800 | 3 |
| Ex. 56 | Olivem 1000 | 3 |
| Ex. 57 | Montanov L | 3 |
| Ex. 58 | Montanov 68 | 3 |
| Ex. 59 | Lipoid S 75-3 | 3 |
| Ex. 60 | Tegocare 450 | 3 |
| Ex. 61 | Span 60 | 3 |
| Ex. 62 | Tween 20 | 3 |
| Ex. 63 | Amphisol K | 3 |

TABLE 27

| | SPF (before UV irradiation) | SPF (after UV irradiation) | Change in SPF value | Change in SPF (%) |
|---|---|---|---|---|
| Ex. 54 | 45.56 ± 12.36 | 50.12 ± 11.04 | 4.56 | 10.01 |
| Ex. 55 | 40.72 ± 8.03 | 44.4 ± 7.84 | 3.68 | 9.04 |
| Ex. 56 | 49.73 ± 9.95 | 55.05 ± 9.65 | 5.32 | 10.70 |
| Ex. 57 | 46.24 ± 9.79 | 49.22 ± 9.09 | 2.98 | 6.44 |
| Ex. 58 | 48.17 ± 9.6 | 52.67 ± 9.57 | 4.50 | 9.34 |
| Ex. 59 | 51.21 ± 8.67 | 58.04 ± 10.14 | 6.83 | 13.34 |
| Ex. 60 | 35.16 ± 7.48 | 46.72 ± 8.48 | 11.56 | 32.88 |
| Ex. 61 | 40.93 ± 7.62 | 48.73 ± 7.86 | 7.80 | 19.06 |
| Ex. 62 | 34.13 ± 7.53 | 34.95 ± 8.39 | 0.82 | 2.40 |
| Ex. 63 | 24.78 ± 4.88 | 26.47 ± 4.99 | 1.69 | 6.82 |

It can be seen that even when an emulsifier suitable for an oil-in-water formulation is present, the effect of the present disclosure is maintained.

Test Example 13: UV Protection Effect Depending on Polymer

The cosmetic products for UV protection were obtained according to the composition of the following Table 28 and Table 29. Part A and Part B were prepared individually and warmed to 75° C. While Part B was introduced gradually to Part B, emulsification was carried out for 5 minutes by using a homo-mixer, followed by cooling to 30° C. Each of the resultant samples was determined in terms of SPF value before and after UV irradiation in the same manner as Test Example 1. The results are shown in the following Table 30.

TABLE 28

| | | | Examples 64-68 | Examples 69-71 |
|---|---|---|---|---|
| A | 1 | OMC | 7.00 | 7.00 |
| | 2 | IMC | 9.00 | 9.00 |
| | 3 | BEMT | 2.00 | 2.00 |
| | 4 | MT-100TV | 2.00 | 2.00 |
| | 5 | Lipoid S 75-3 | 3.00 | 3.00 |
| B | 6 | Purified water | 79.70 | 79.75 |
| | 7 | 1,2-Hexanediol | 2.00 | 2.00 |
| | 8 | polymer | 0.30 | 0.15 |
| | 9 | tris amino ultra pc | 0.00 | 0.10 |

TABLE 29

| | Polymer | Content |
|---|---|---|
| Ex. 64 | comedia SP | 0.3 |
| Ex. 65 | Aristoflex AVC | 0.3 |
| Ex. 66 | volarest | 0.3 |
| Ex. 67 | sepimax gen | 0.3 |
| Ex. 68 | Keltrol F | 0.3 |
| Ex. 69 | pemulene TR2 | 0.15 |
| Ex. 70 | C 980 | 0.15 |
| Ex. 71 | Utrez-21 | 0.15 |

TABLE 30

| | SPF (before UV irradiation) | SPF (after UV irradiation) | Change in SPF value | Change in SPF (%) |
|---|---|---|---|---|
| Ex. 64 | 44.81 ± 8.19 | 48.47 ± 10.33 | 3.66 | 8.17 |
| Ex. 65 | 43.9 ± 6.07 | 47.49 ± 5.34 | 3.59 | 8.18 |
| Ex. 66 | 39.13 ± 6.39 | 42.76 ± 7.63 | 3.63 | 9.28 |
| Ex. 67 | 33.09 ± 1.75 | 36.86 ± 2.27 | 3.77 | 11.39 |
| Ex. 68 | 31.5 ± 3.64 | 33.9 ± 5.3 | 2.68 | 9.30 |
| Ex. 69 | 28.81 ± 2.21 | 31.49 ± 2.77 | 2.40 | 7.62 |
| Ex. 70 | 44.13 ± 6.45 | 48.53 ± 9.22 | 4.40 | 9.97 |
| Ex. 71 | 41.85 ± 4.91 | 44.71 ± 5.68 | 2.86 | 6.83 |

It can be seen that even when a thickener used for an oil-in-water formulation is present, the effect of the present disclosure is maintained.

Test Example 14: UV Protection Effect Depending on Type of Emulsifier in O/W Formulation The cosmetic products for UV protection were prepared by using various types of emulsifiers as shown in the following Table 32 according to the composition of the following Table 31 as follows. The ingredients of Part A were mixed thoroughly at 75° C. Ingredient 7 and Ingredient 8 were introduced to Ingredient 6 and dispersed therein for 30 minutes by using Disper. The remaining ingredients of Part B were introduced thereto and the resultant mixture warmed to 75° C. While Part A was introduced gradually to Part B, emulsification was carried out for 10 minutes by using a homo-mixer, followed by cooling to 30° C. Each of the resultant samples was determined in terms of SPF value before and after UV irradiation in the same manner as Test Example 1. The results are shown in the following Table 33.

TABLE 31

| A | 1 | OMC | 7.00 |
|---|---|---|---|
|   | 2 | IMC | 9.00 |
|   | 3 | BEMT | 2.00 |
|   | 4 | MT-100TV | 2.00 |
|   | 5 | Emulsifier | 3.00 |
| B | 6 | Purified water | to 100 |
|   | 7 | Sodium polyacrylate | 0.50 |
|   | 8 | Xanthan gum | 0.10 |
|   | 9 | Tinosorb S lite aqua | 5.00 |
|   | 10 | Panthenol | 1.00 |
|   | 11 | EDTA 3NA | 0.02 |
|   | 12 | 1,2-Hexanediol | 2.00 |

* OMC: Ethylhexyl methoxycinnamate/IMC: Isoamyl p-methoxycinnamate/BEMT: Bis-ethylhexyloxyphenol methoxyphenyl triazine

TABLE 32

| | Emulsifier |
|---|---|
| Ex. 72 | Sodium polyacrylate |
| Ex. 73 | Cetearyl olivate, Sorbitan olivate |
| Ex. 74 | C14-22 alcohols, C12-20 alkyl glucoside |
| Ex. 75 | Hydrogenated lecithin |
| Ex. 76 | Ceteareth-6 olivate |
| Ex. 77 | Polyglyceryl-3 methyl glucose distearate |
| Ex. 78 | Polysorbate 20 |
| Comp. Ex. 36 | Polysorbate 60 |
| Ex. 79 | Potassium cetyl phosphate |

TABLE 33

| | SPF (before UV irradiation) | SPF (after UV irradiation) | Change in SPF value | Change in SPF (%) |
|---|---|---|---|---|
| Ex. 72 | 37.57 ± 4.89 | 44.19 ± 5.41 | 6.62 | 17.62 |
| Ex. 73 | 52.29 ± 4.53 | 59.85 ± 5.18 | 7.56 | 14.46 |
| Ex. 74 | 52.47 ± 3.36 | 57.86 ± 7.61 | 5.39 | 10.27 |
| Ex. 75 | 42.5 ± 4.12 | 56.84 ± 4.74 | 14.34 | 33.74 |
| Ex. 76 | 52.73 ± 3.79 | 53.65 ± 3.73 | 0.92 | 1.74 |
| Ex. 77 | 43.27 ± 4.92 | 44 01 ± 4.75 | 0.74 | 1.71 |
| Ex. 78 | 51.09 ± 5.41 | 53,64 ± 7.44 | 2.55 | 4.99 |
| Comp. Ex. 36 | 44.36 ± 7.54 | 39.45 ± 8.43 | −4.91 | −11.07 |
| Ex. 79 | 51.96 ± 4.37 | 53 ± 4.57 | 1.04 | 2.00 |

While the emulsifiers used in Examples 72-79 increase UV protection effect significantly, the emulsifier used in Comparative Example 36 cannot increase UV protection effect.

What is claimed is:

1. A cosmetic composition for UV protection, comprising a sunscreen having a methoxycinnamate structure and 5 wt % or less of polar oil based on the total weight of the composition,
wherein the sunscreen having a methoxycinnamate structure and the polar oil are in a weight ratio from 1:0.01 to 1:0.4,
wherein the sunscreen having a methoxycinnamate structure comprises at least one selected from the group consisting of ethylhexyl methoxycinnamate, isoamyl p-methoxycinnamate and cinoxate, and
wherein the polar oil comprises at least one selected from the group consisting of cetylethyl hexanoate, caprylic/capric glycerides, phenethyl benzoate, dicaprylyl carbonate, C12-C15 alkyl benzoates and octocrylene.

2. The cosmetic composition for UV protection according to claim 1, wherein the sunscreen having a methoxycinnamate structure is used in an amount of 2-30 wt % based on the total weight of the composition.

3. The cosmetic composition for UV protection according to claim 1, wherein the sunscreen having a methoxycinnamate structure and the polar oil are in a weight ratio (sunscreen having a methoxycinnamate structure:polar oil) of 1:0.01.

4. The cosmetic composition for UV protection according to claim 1, which further comprises hydrocarbon oil.

5. The cosmetic composition for UV protection according to claim 4, wherein the hydrocarbon oil is used in an amount of 5-30 wt % based on the total weight of the composition.

6. A cosmetic composition for UV protection, comprising a sunscreen having a methoxycinnamate structure and hydrocarbon oil,
wherein the sunscreen having a methoxycinnamate structure and the hydrocarbon oil are in a weight ratio from 1:0.05 to 1:0.93,
wherein the sunscreen having a methoxycinnamate structure comprises at least one selected from the group consisting of ethylhexyl methoxycinnamate, isoamyl p-methoxycinnamate and cinoxate, and
wherein the hydrocarbon oil comprises at least one selected from the group consisting of liquid paraffin, light liquid isoparaffin, heavy liquid isoparaffin, Vaseline, n-paraffin, mineral oil, isoparaffin, isododecane, isohexadecane, polyisobutylene, hydrogenated polyisobutylene, polybutene, ozokerite, ceresin, microcrystalline wax, paraffin wax, polyethylene wax, polyethylene/polypropylene wax, squalane, squalene, pristane and polyisoprene.

7. The cosmetic composition for UV protection according to claim 6, wherein the sunscreen having a methoxycinnamate structure is used in an amount of 2-30 wt % based on the total weight of the composition.

8. The cosmetic composition for UV protection according to claim 6, wherein the hydrocarbon oil is used in an amount of 5-30 wt % based on the total weight of the composition.

9. The cosmetic composition for UV protection according to claim 6, wherein the sunscreen having a methoxycinnamate structure and the hydrocarbon oil are in a weight ratio (sunscreen having a methoxycinnamate structure:hydrocarbon oil) of 1:0.2.

10. A cosmetic composition for UV protection, comprising a sunscreen having a methoxycinnamate structure and polar oil, wherein the sunscreen is isoamyl p-methoxycinnamate,
wherein the content of the polar oil is equal to or smaller than the content of isoamyl p-methoxycinnamate, and
wherein the polar oil comprises at least one selected from the group consisting of cetylethyl hexanoate, caprylic/capric glycerides, phenethyl benzoate, dicaprylyl carbonate, C12-C15 alkyl benzoates and octocrylene.

11. The cosmetic composition for UV protection according to claim 10, which has an oil-in-water formulation.

12. The cosmetic composition for UV protection according to claim 10, wherein the sunscreen having a methoxycinnamate structure is used in an amount of 2-30 wt % based on the total weight of the composition.

13. The cosmetic composition for UV protection according to claim 10, wherein the sunscreen having a methoxycinnamate structure further comprises ethylhexyl methoxycinnamate, cinoxate or a mixture thereof.

14. The cosmetic composition for UV protection according to claim 10, which comprises isoamyl p-methoxycinnamate and polar oil at a weight ratio (isoamyl p-methoxycinnamate:polar oil) of 1:0.01-7.

15. The cosmetic composition for UV protection according to claim 10, which further comprises nonpolar oil.

\* \* \* \* \*